United States Patent [19]
Kelly et al.

[11] Patent Number: 5,834,503
[45] Date of Patent: Nov. 10, 1998

[54] METHODS TO TREAT ARTERIAL PLAQUE

[75] Inventors: Barbara Kelly; Julia Levy; Philippe Maria Clotaire Margaron, all of Vancouver, Canada

[73] Assignee: QLT Phototherapeutics, Inc., Vancouver, Canada

[21] Appl. No.: 663,890

[22] Filed: Jun. 14, 1996

[51] Int. Cl.$^6$ ....................................................... A61K 31/40
[52] U.S. Cl. ........................................... 514/410; 514/824
[58] Field of Search ............................................... 514/410

[56] References Cited

U.S. PATENT DOCUMENTS

| | | |
|---|---|---|
| 4,512,762 | 4/1985 | Spears . |
| 4,577,636 | 3/1986 | Spears . |
| 4,920,143 | 4/1990 | Levy et al. . |
| 5,053,423 | 10/1991 | Liu .......................................... 514/410 |
| 5,095,030 | 3/1992 | Levy et al. . |
| 5,150,717 | 9/1992 | Rosen et al. . |
| 5,171,749 | 12/1992 | Levy et al. . |
| 5,399,583 | 3/1995 | Levy et al. . |
| 5,422,362 | 6/1995 | Vincent et al. ........................... 514/410 |

FOREIGN PATENT DOCUMENTS

| | | |
|---|---|---|
| WO 94/00095 | 6/1994 | WIPO . |
| WO 95/03795 | 2/1995 | WIPO . |

OTHER PUBLICATIONS

Munro, J.M. et al., "The Pathogenesis of Atherosclerosis: Atherogenesis and Inflammation," *Laboratory Investigation* (1988) 58(3):249–250.

*Primary Examiner*—Kevin E. Weddington
*Assistant Examiner*—M. Moezie
*Attorney, Agent, or Firm*—Morrison & Foerster LLP

[57] ABSTRACT

A method to prevent or inhibit the development of arterial plaque, comprising the steps of:
  a. administering to a subject an amount of a green porphyrin compound effective to prevent or inhibit said development; and
  b. allowing the inhibition to occur in the absence of irradiation with light absorbed by the green porphyrin,
or a pharmaceutical composition for preventing or inhibiting the development of arterial plaque. The composition comprises:
  a. an amount of a green porphyrin compound effective to prevent or inhibit the development when administered to a subject in need of such treatment, even in the absence of irradiation with light absorbed by said the green porphyrin; and
  b. a pharmaceutically acceptable excipient.

The administration of the green porphyrin need not be accompanied by any purposeful irradiation with light.

20 Claims, 3 Drawing Sheets

METHODS TO TREAT ARTERIAL PLAQUE

BACKGROUND OF THE INVENTION

1. Field of the Invention

The present invention relates to the treatment of fatty deposits in atherosclerotic blood vessels. In particular, the invention relates to the prevention or inhibition of arterial plaque by administering a green porphyrin compound. Unlike standard photodynamic protocols, no purposeful irradiation with light is needed to effect the desired inhibition.

2. Description of the Related Art

Atherosclerosis is an arterial disease in which fatty substances (lipids) accumulate in the intima or inner media, the innermost membranes encompassing the lumen of the artery. The resulting lesions are referred to as atherosclerotic plaque. Clinical symptoms finally occur because the growing mass of the atherosclerotic plaque gradually reduces blood flow through the involved artery, thereby compromising the tissue or organ function distal to it. Atherosclerosis and its complications, such as myocardial infarction, stroke, and peripheral vascular diseases, remain major causes of morbidity and mortality in the Western World. Coronary heart disease alone has been reported to account for over half a million deaths in the United States annually.

Figure 3:
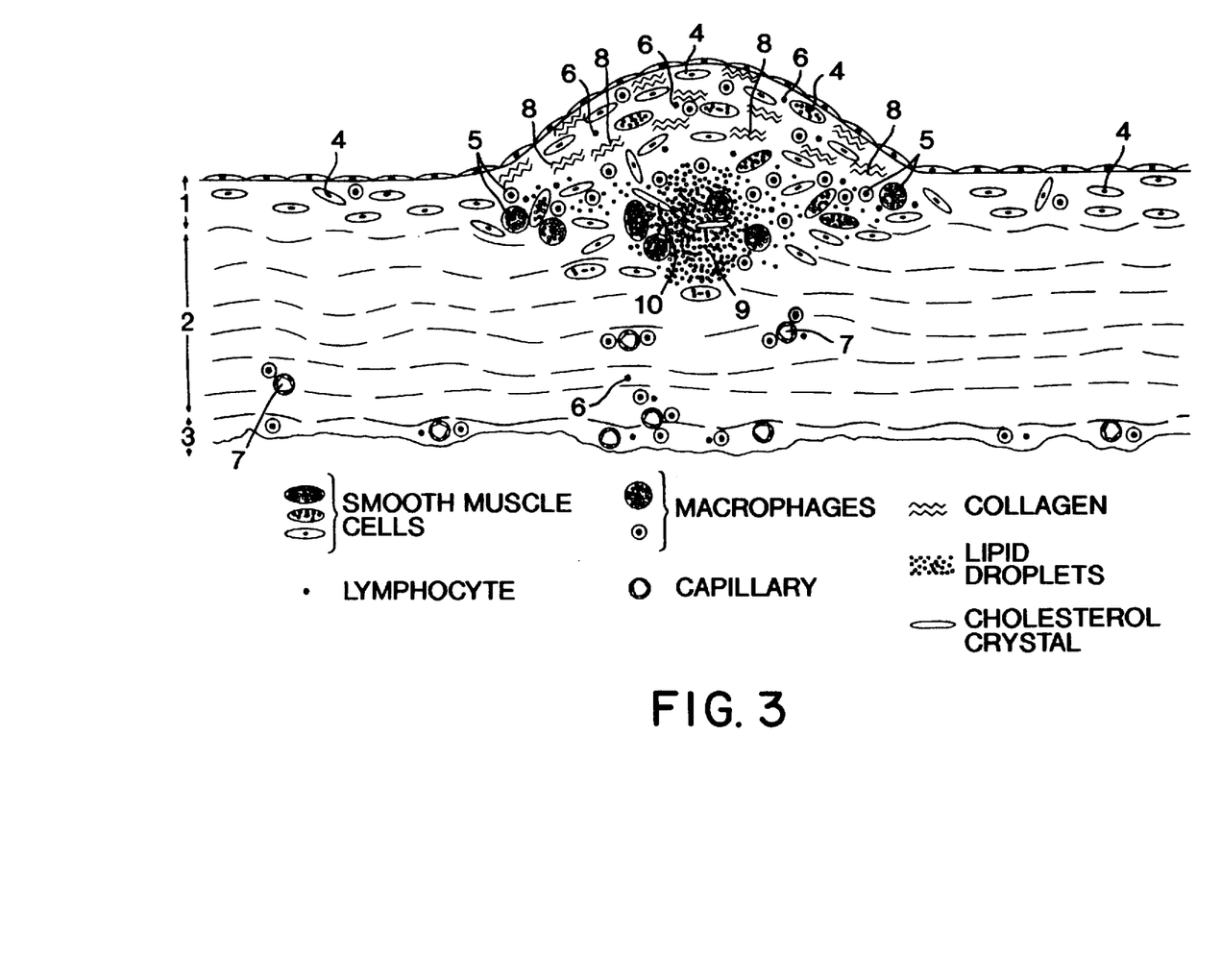
FIG. 3 represents a cross-sectional view of an atherosclerotic plaque.

The fundamental lesion of atherosclerosis is the atheromatous or fibrofatty plaque, which causes narrowing of the artery, predisposes to thrombosis, calcifies, leads to weakening of the muscle, and causes aneurysmal dilation. Atherosclerotic plaques are approximately rounded, raised lesions, usually off-white to white in color superficially, and perhaps a centimeter in diameter. The center of larger plaques may exude a yellow, grumous fluid. A typical cellular plaque is shown in FIG. 3 and consists of:

1. a fibrous cap composed mostly of smooth muscle cells with a few leukocytes and relatively dense connective tissue, which contains elastin, collagen fibrils, proteoglycans, and basement membrane;
2. a cellular area beneath and to the side of the cap consisting of a mixture of macrophages, smooth muscle cells, and T lymphocytes; and
3. a deeper "necrotic core" containing cellular debris, extracellular lipid droplets, and cholesterol crystals. Munro et al., "Biology of Disease; The Pathogenesis of Atherosclerosis: Atherogenesis and Inflammation", *Laboratory Investigation* 58:3, 249–50 (1988).

Left unchecked, the formation of plaque can result in the complete occlusion of the artery and severe clinical consequences. For example, when complicated, the lesion becomes a calcified fibrous plaque containing various degrees of necrosis, thrombosis and ulceration. With increasing necrosis and accumulation of cell debris, the arterial wall progressively weakens, and rupture of the intima can occur, causing aneurysm and hemorrhage. Arterial emboli can form when fragments of plaque dislodge into the lumen. Stenosis and impaired organ function result from gradual occlusion as plaques thicken and thrombi form.

The treatment of atherosclerosis generally focuses on the care of patients suffering from atherosclerotic complications and typically follows one of four basic approaches: (1) the diseased vascular segments may be replaced with prosthetic or natural grafts, going as far as whole heart transplantation; (2) drugs, such as antiarrhythmic agents, anticoagulants and plasma lipid lowering agents, may be administered to enable the patient to live with the conditions; (3) the plaque may be physically reduced in size by the use of a balloon catheter in angioplasty; or (4) photodynamic therapy may be used which couples the administration of photosensitive agent and subsequent irradiation with light to excite the photosensitizer, thus producing a cytotoxic effect. Spears, U.S. Pat. Nos. 4,512,762, issued 23 Apr. 1985 and U.S. Pat. No. 4,566,636 issues 25 Mar. 1986.

In photodynamic therapy, the photosensitizers used are capable of localizing in malignant cells, either by natural tendency or because they have been intentionally targeted to a specific type of tissue, or both. When irradiated, they may be capable of fluorescing and, thus, may be useful in diagnostic methods related to detecting target tissue. However, even more importantly, the photosensitizer has the capacity, when irradiated with light at a wavelength which the compound absorbs, of causing a cytotoxic effect against whatever cells or other tissue in which the photosensitizer has localized. Although not yet definitively established, it is thought that this cytotoxic effect is due to the formation of singlet oxygen upon irradiation.

In most photodynamic therapy protocols, a method must be found for the irradiating light to reach the targeted tissue where the photosensitizer has been localized. This is particularly difficult when the wavelength of irradiation that is required to activate the compound is in the range of about 630 nm, a wavelength that is readily absorbed by natural chromophores in blood and other surrounding tissues. In one technique, the patient must be catheterized with a light-emitting catheter being inserted into the diseased artery or other vessel so that the light-emitting portion of the catheter is adjacent to the atherosclerotic plaque. For example, a light-emitting balloon catheter may be used to displace light-opaque blood between the external balloon surface and the atherosclerotic plaque by inflation of the balloon. Alternatively, a form of "liquid light" may be injected into the vascular tree such that the "liquid light", which mixes freely with blood or a blood replacement, perfuses the diseased artery. Spears, U.S. Pat. No. 4,512,762.

In another method, to keep dosages low and decrease the patient's sensitization to light, a preferred group of "green porphyrins" have made it possible to conduct photodynamic therapy with light having a wavelength range outside of that normally strongly absorbed by the blood or other normal tissues, specifically around 670–780 nm. In addition to providing an effective in vivo treatment at lower concentrations and reducing hypersensitivity of non-target tissues, a greater depth of penetration by the irradiating light is also usually achieved. Because these photosensitizers appear green in color rather than red, they have been nicknamed "green porphyrins." It is known that green porphyrins can be used to detect and treat atherosclerotic plaques in a photodynamic therapy protocol. See, for example, Levy et al., U.S. Pat. No. 5,399,583 issued 21 Mar. 1995 (column 2, lines 14–15); Levy et al., U.S. Pat. No. 4,920,143 issued 24 Apr. 1990 (column 10, lines 58–59); Levy et al., U.S. Pat. No. 5,095,030 issued 10 Mar. 1992 (column 2, lines 8–9 and column 15, lines 29–30); and Levy et al., U.S. Pat. No. 5,171,749 issued 15 Dec. 1992 (column 2, lines 12–13 and column 18, lines 1–4 and 35–47).

It has also been found that green porphyrins can exert certain "dark effects", which take place without any purposeful irradiation at all with photoactivating light. For example, it has been found that administration of a green porphyrin following a vascular intervention procedure, such as angioplasty, can significantly reduce the proliferation of smooth muscle cells that typically builds up in the intima to cause "restenosis" or "intimal hyperplasia". See Vincent et al., U.S. Pat. No. 5,422,362 issued 6 Jun. 1995. Moreover, it has been found that the immune response to a specific antigen may be modulated and that the intercellular communication that results in thrombosis or blood clot formation in the bloodstream by may be interfered with by administering green porphyrins in the absence of light, as described in co-pending application Ser. No. 08/374,158 filed 13 Jan. 1995, now pending.

However, until now, the use of green porphyrins to treat fatty atherosclerotic plaques has been limited to a photodynamic therapy protocol, which requires that the administration of the photosensitizer be followed by the irradiation of the inner membrane of the blood vessel with light having a wavelength capable of stimulating the green porphyrin to produce a cytotoxic effect. It would thus be advantageous to provide a treatment to inhibit or prevent arterial plaque that would completely avoid the necessity for specialized light-emitting devices. It has now been discovered that green porphyrins may be used to prevent or inhibit the development of arterial plaque without having purposeful light exposure of any kind.

SUMMARY OF THE INVENTION

According to the present invention, there has been developed a method to prevent or inhibit the development of arterial plaque, comprising the steps of:

a. administering to a subject an amount of a green porphyrin compound effective to prevent or inhibit said development; and b. allowing said inhibition to occur in the absence of irradiation with light absorbed by said green porphyrin.

The invention also concerns a pharmaceutical composition for preventing or inhibiting the development of arterial plaque. The composition comprises:

a. an amount of a green porphyrin compound effective to prevent or inhibit said development when administered to a subject in need of such treatment, even in the absence of irradiation with light absorbed by said Gp; and b. a pharmaceutically acceptable excipient.

As a result of the invention, the administration of the green porphyrin, surprisingly, need not be accompanied by irradiation with light absorbed by the green porphyrin administered. Rather, the treatment is typically performed without purposeful irradiation with light of any type.

BRIEF DESCRIPTION OF THE DRAWINGS

The present invention will be more clearly understood by referring to the following drawings, in which.

DETAILED DESCRIPTION OF THE INVENTION

Atherosclerosis tends to involve large and medium-sized muscular arteries. Most commonly affected are the aorta and the iliac, femoral, coronary, carotid, basilar, vertebral and cerebral arteries.

As used herein, "atherosclerotic arterial plaque" is defined as a pathophysiological phenomenon which is accompanied by the proliferation of fatty or lipid deposits within the intima or the inner media, the innermost layers encompassing the lumen of the artery.

As shown in the cross-section schematic of FIG. 3, an atherosclerotic plaque occurs within the intima 1 or the media 2 (medial smooth muscle cells not shown), both of which extend over the adventitia 3, the outer coat of the artery. An overlaying endothelial layer overlies the plaque. The fibromuscular "cap" portion of the plaque contains smooth muscle cells 4, macrophages 5, and collagen bands 8. Underneath this is the "core" with abundant extracellular lipid droplets 9, "foam" cells whose cytoplasm is filled with lipid droplets, cholesterol crystals 10, and necrotic cellular debris. Macrophages 5 are widely distributed, and lymphocytes 6 can be found in the cap and to the sides of the core. Adventitial capillaries 7 gravitate toward the intimal lesion. Munro et al., "Biology of Disease; The Pathogenesis of Atherosclerosis: Atherogenesis and Inflammation", *Laboratory Investigation* 58:3, 249–50 (1988).

The Green Porphyrins

The green porphyrins useful in the method of the invention are described in detail in Levy et al., U.S. Pat. No. 5,171,749 issued 15 Dec. 1992, which is incorporated herein by reference. "Green porphyrins" refer to porphyrin derivatives obtained by reacting a porphyrin nucleus with an alkyne in a Diels-Alder type reaction to obtain a monohydrobenzoporphyrin. Typically, green porphyrins are selected from a group of porphyrin derivatives obtained by Diels-Alder reactions of acetylene derivatives with protoporphyrin under conditions that promote reaction at only one of the two available conjugated, nonaromatic diene structures present in the protoporphyrin-IX ring system (rings A and B).

Figure 1:
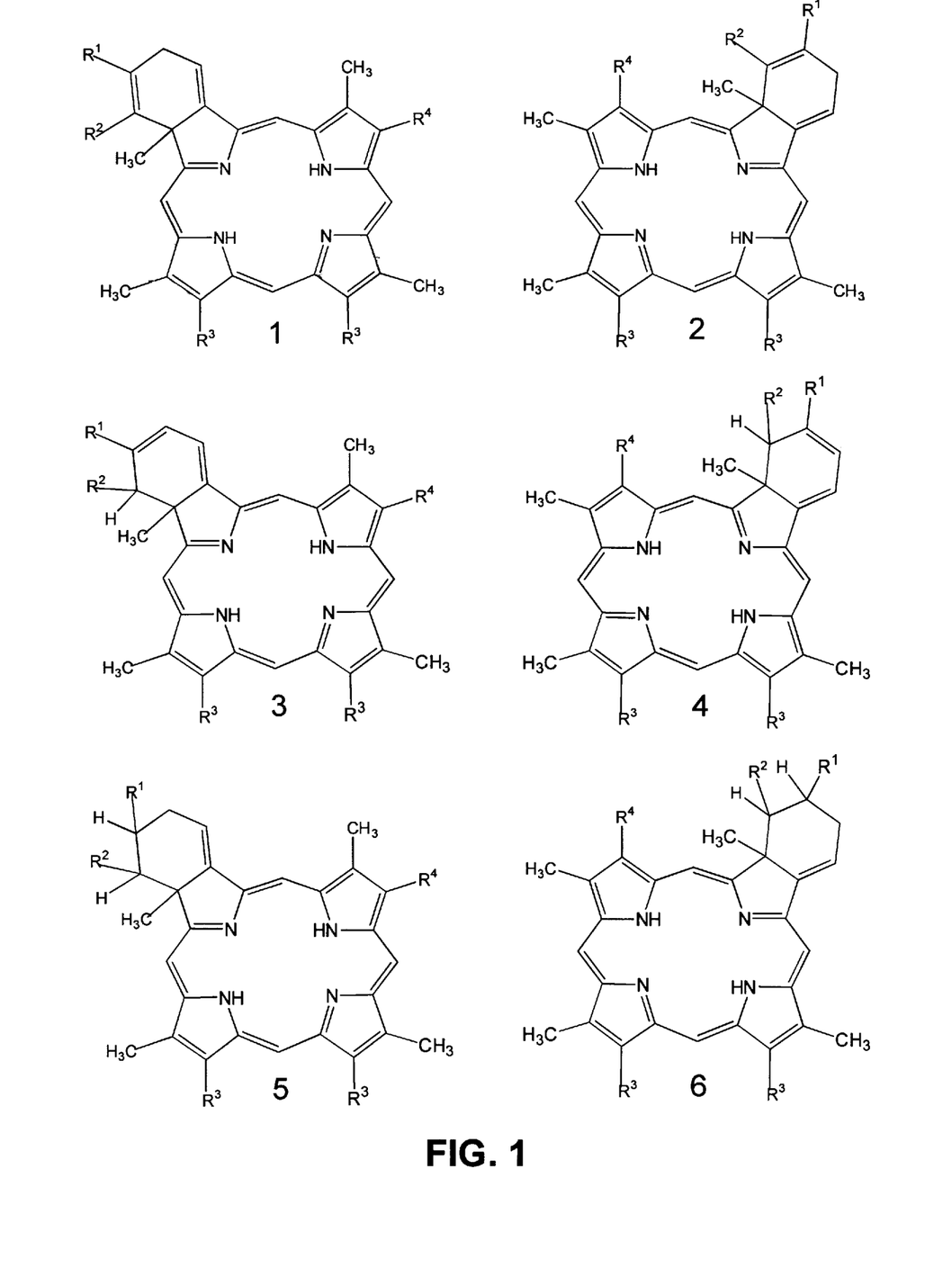
FIG. 1 shows the formulas of typical green porphyrins useful in the method and composition of the invention.

Several structures of typical green porphyrins are shown in FIG. 1. The Diels-Alder reaction initially results in the formation of a cyclohexadiene—referred to herein as "hydrobenzo"—fused to the A or B pyrrolic ring, as shown in formulas 1 and 2. Rearrangement of the π system in the hexadiene ring results in the formation of compounds of formulas 3 and 4, and reduction provides compounds of formulas 5 and 6. These compounds are shown in formulas 1–6 with hydrogen occupying the internal ring nitrogens. However, it is to be understood that the metalated forms, in which a cation replaces one or both of these hydrogens, can also be used. The preparation of the green porphyrin compounds useful in this invention is described in detail in U.S. Pat. No. 5,095,030, which is incorporated herein by reference.

For convenience, an abbreviation of the term hydromonobenzoporphyrin derivative—"BPD"—is generally used to refer to compounds of formulas 3 and 4 of FIG. 1. Compounds of the formulas 3 and 4 and mixtures thereof are particularly preferred.

As shown in FIG. 1, $R^1$, $R^2$, $R^3$ and $R^4$ are non-interfering substituents that do not appreciably affect the activity of the compound in the method and composition of the invention. More specifically, the term "non-interfering substituents" is used to mean substituents that do not destroy the ability of the green porphyrin to prevent or inhibit arterial plaque. For the compounds of FIGS. 1 and 2, generally, $R^1$ and $R^2$ are each, independently, moderately electron-withdrawing substituents or any other activating substituents that are not sufficiently electron-withdrawing to result in the Diels-Alder reaction proceeding with both A and B rings, rather than only one. Examples of suitable $R^1$ and $R^2$ groups include carbalkoxy (2–6C), alkyl (1–6C) sulfonyl or aryl (6–10C) sulfonyl, aryl (6–10C), cyano, and —$CONR^5CO$— where $R^5$ is aryl (6–10C) or alkyl (1–6). One of $R^1$ and $R^2$ may also be hydrogen, so long as the other is an electron-withdrawing substituent of sufficient strength to facilitate the Diels-Alder reaction. Most commonly, $R^1$ and $R^2$ are carbalkoxy groups, preferably methyl or ethyl carboxy esters. Preferred compounds are those in which $R^1$ and $R^2$ are the same and are carbalkoxy, particularly carboethoxy.

As used herein, the term "carboxy" is, as conventionally defined, —COOH, while "carbalkoxy" represents —COOR where R is alkyl. "Carboxyalkyl" refers to the substituent —R'—COOH where R' is alkylene. "Carbalkoxyalkyl" refers to —R'—COOR where R' and R are alkylene and alkyl respectively. "Alkyl" generally represents a saturated straight or branched chain hydrocarbyl moiety of 1–6 carbon atoms, such as methyl, n-hexyl, 2-methylpentyl, t-butyl, n-propyl, and so forth. "Alkylene" is the same as "alkyl" except that the group is divalent rather than monovalent. "Aryl" represents a phenyl group, optionally substituted with 1–3 substituents, which may be independently selected from the group consisting of halo, such as fluoro, chloro, bromo or iodo; lower alkyl (1–4C); and lower alkoxy (1–4C). "Aryl" or "alkyl sulfonyl" groups have the formula —$SO_2R$ where R is alkyl or aryl as defined above.

$R^3$ is independently a ω-carboxyalkyl group (2–6C) or a salt, amide, ester or acylhydrazone thereof, or is alkyl (1–6C). Preferably, $R^3$ is 2-carboxyethyl or the alkyl ester thereof, and $R^4$ is vinyl. These embodiments, however, are preferred because of the availability of native porphyrins, rather than being mandated by considerations of biological efficacy. As shown in FIG. 1, adducts formed by the reaction of $R^1$—C≡C—$R^2$ with a protoporphyrin-IX ring system (where $R^3$ is a protected form of 2-carboxyethyl, such as 2-carbomethoxyethyl or 2-carboethoxyethyl, and $R^4$ is —CH=$CH_2$) are compounds of the formulas 1 and 2. Compounds of formula 1 result from the addition to the A ring, and compounds of formula 2 result from the addition to the B ring.

Convenient starting materials for the green porphyrin compounds of the invention include the naturally-occurring porphyrins where $R^3$ is either —$CH_2CH_2COOH$ or —$CH_2CHRCOOR$ where R is alkyl (1–6C). However, the exact nature of $R^3$, unless it contains a π-bond conjugated to ring π-bond, is ordinarily not relevant to the progress of the Diels-Alder reaction or to the effectiveness of the resulting product. $R^3$ can thus be any one of a wide variety of groups such as, for example, lower alkyl (1–4C); and ω-carboxyalkyl (2–6C) and the esters and amides thereof. The $R^3$ substituent may also be substituted with halogen, such as fluoro, chloro, bromo or iodo; or with other nonreactive substituents.

When $R^3$ is $CH_2CHRCOOR$, it has been found advantageous to hydrolyze, or partially hydrolyze, the esterified carboxy group. Typically, the hydrolysis at the $R^3$-position conveniently occurs at a much faster rate than that of the ester groups of $R^1$ or $R^2$. Further, the solubility and biodistribution characteristics of the resulting compounds are more desirable than those of the unhydrolyzed form. Hydrolysis results in the diacid or monoacid products (or their salts).

In compounds of formulas 1 and 2, $R^4$ is usually —CH=$CH_2$, at least initially, but this vinyl group is readily derivatized to other embodiments of $R^4$ by the addition to, or oxidation of, the vinyl ring substituent of ring B or A in formula 1 or 2 respectively. Thus, $R^4$ can be any one of a wide variety of substituents that are consistent with that formed by a facile addition reaction. For example, an exemplary addition reagent may be of the form HX where H is added to the carbon adjacent to the ring to provide an $R^4$-position having the formula:

Thus, in one embodiment, one of the added substituents is a hydrogen, and the other one is selected from the group consisting of hydrogen; halo such as fluoro, chloro, bromo or iodo; hydroxy; lower alkoxy; amino; amide; sulfhydryl; or an organosulfide. For example, the Markovnikov addition of water provides a substituent structure analogous to a hematoporphyrin ring system at the relevant ring. The vinyl group can also be oxidized to obtain, as a substituent in the $R^4$-position, —$CH_2OH$, —CHO, or COOH or its salts or esters. The addition or oxidation products can themselves also be substituted if the added substituents are functional leaving groups. For example, when Br is a substituent, it may be replaced by such moieties as —OH, —OR where R is alkyl (1–6C) as described above, halo, —$NH_2$, —NHR, —$NR_2$ and the like.

Thus, in general, $R^4$ represents any substituents to which the vinyl group —CH=$CH_2$ is readily converted by cleavage or addition, and further substituents formed by the reaction of leaving good groups with additional moieties. Preferably, however, $R^4$ is vinyl (—CH=$CH_2$); —$CHOR^4$ where $R^4$ is H or alkyl (1–6C), optionally substituted with a hydrophilic substituent such as —$CH_2OH$; —CHO; —$COOR^4$ such as COOH or —$COOCH_3$; —$CH(OR^{4'})CH_3$ such as —$CH(OH)CH_3$ or —$CH(OCH_3)CH_3$; —$CH(OR^{4'})CH_2OR^{4'}$; —$CH(OH)CH_2OH$; —$CH(SR^{4'})CH_3$ such as —$CH(SCH_3)CH^3$ and the disulfide thereof; —$CH(NR^{4'})CH_3$; —$CH(CN)CH_3$; —CH(pyridinium bromide)$CH_3$; —$CH(COOR^{4'})CH_3$; —$CH(COOCR^{4'})CH_3$; —$CH_2(halo)CH_3$ such as —$CHBrCH_3$; or —CH(halo)$CH_2$(halo). Alternatively, $R^4$ can be an organic group of less than 12 carbon atoms resulting from the direct or indirect derivatization of vinyl. Or $R^4$ can provide additional porphyrin or porphyrin-related ring systems, such as a group containing from 1–3 tetrapyrrole-type nuclei of the formula —L—P, as defined below. Those compounds in which $R^4$ is —CH=$CH_2$, —$CH(OH)CH_3$, —CH(halo)$CH_3$, or a group containing 1–3 tetrapyrrole-type nuclei of the formula —L—P, as defined below, are preferred.

As used herein, the term "tetrapyrrole-type nucleus" represents a four-ring system of the skeleton:

or a salt, ester, amide, or acylhydrazone thereof, which is highly conjugated. It includes the porphyrin system, which is in effect a completely conjugated system; the chlorin system, which is in effect a dihydro form of the porphyrin; and the reduced chlorin system, which is a tetrahydro form of the conjugated porphyrin system. When "porphyrin" is specified, the completely conjugated system is indicated.

Green porphyrins are effectively a dihydro form of the porphyrin system.

In one embodiment, the substituent $R^4$ includes at least one additional tetrapyrrole-type nucleus. The resulting compounds of the invention are dimers or oligomers in which at least one of the tetrapyrrole-type ring systems is a green porphyrin. Linkage between the green porphyrin moiety at the $R^4$-position to an additional tetrapyrrole-type ring system may be by an ether, amine or vinyl linkage. Porphyrin ring systems having two available substituent positions (in both A and B rings) corresponding to $R^4$ can be additionally derivatized, as explained below.

When R4 is "—L—P," —L— is selected from the group consisting of:

and P is a porphyrin structure or a second green porphyrin of the formulas 1–6 shown in FIG. 1, except that any second R4 group is replaced by L above.

(It is also understood that, when —L— is of the formula (e) or (f) shown above, the ring system to which the double bond is attached will have a resonance system corresponding to in the ring to which the double bond is attached, as shown.)

The hydro-monobenzoporphyrins that directly result from the Diels-Alder reaction described above can also be isomerized to the BPD compounds of formulas 3 and 4 of FIG. 1. The depictions of compounds 3 and 4 in FIG. 1 do not show the relative position of the exocyclic methyl group (ring A formula 3 and ring B of formula 4) with respect to the $R^2$ substituent. Either isomer is available. Compounds of formulas 3 and 4 are particularly preferred in the methods and compositions of the invention.

In addition, the Diels-Alder products can be selectively reduced by treating with hydrogen in the presence of a catalyst, such as palladium on charcoal, to give the saturated ring analogs, shown as formulas 5 and 6 in FIG. 1, which correspond to the respective Diels-Alder products of rings A and B. The description set forth above with respect to the compounds of formulas 1 and 2 concerning derivatization by conversion of the remaining vinyl substituent ($R^4$) and with respect to the variability of $R^3$ applies as well to the compounds of formulas 3, 4, 5 and 6.

Preferred embodiments of the green porphyrins of the invention are those in which the Diels-Alder product is rearranged and partially hydrolyzed. Even more preferred are the compounds of formulas 3 and 4 (BPD's) in which the carbalkoxy groups in the $R^3$-positions have also been hydrolyzed or partially hydrolyzed. Compounds of the invention that contain —COOH may be prepared as either the free acid or in the form of salts with organic or inorganic bases.

Figure 2:
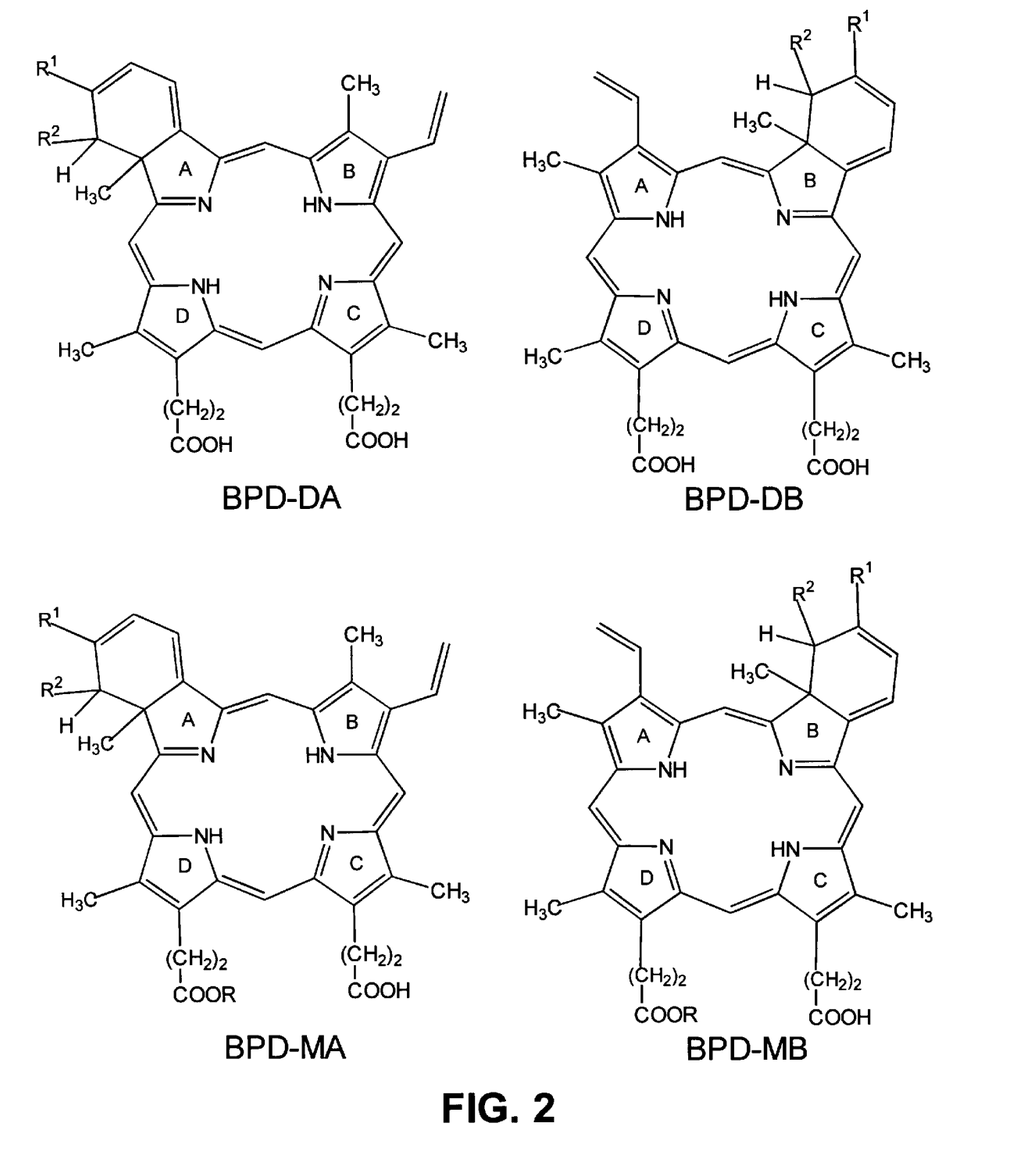
FIG. 2 shows the formulas of four particularly preferred embodiments of the green porphyrins of the invention, BPD-DA, BPD-DB, BPD-MA and BPD-MB.

FIG. 2 shows four particularly preferred compounds of the invention covered by formulas 3 and 4, which are collectively designated as benzoporphyrin derivatives, i.e., BPD-DA, BPD-DB, BPD-MA and BPD-MB. These are hydrolyzed or partially hydrolyzed forms of the rearranged products of formula 3 and 4, wherein one or both of the protected carboxyl groups of $R^3$ have been hydrolyzed. The ester groups at $R^1$ and $R^2$ hydrolyze relatively slowly, so that conversion to the forms shown in FIG. 2 is easily effected. The most preferred of these green porphyrin compounds is BPD-MA.

In FIG. 2, $R^3$ is —$CH_2CH_2COOR^{3'}$ where $R^{3'}$ varies by individual compound. Specifically, in BPD-DA, $R^1$ and $R^2$ are carbalkoxy, $R^{3'}$ is hydrogen, and derivatization is at ring A. BPD-DB is the corresponding compound with derivatization at ring B. BPD-MA represents the partially hydrolyzed form of BPD-DA, and BPD-MB represents the partially hydrolyzed form of BPD-DB. Thus, in these latter compounds, $R^1$ and $R^2$ are carbalkoxy, one $R^{3'}$ is hydrogen, and the other $R^{3'}$ is alkyl (1–6C).

The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates. In addition, mixtures of any two or more of BPD-MA, -MB, -DA and -DB may be used in the methods of and compositions of the invention.

It should be noted that many of the compounds of FIG. 1 contain at least one chiral center and, thus, may exist as optical isomers. The method of the invention can use compounds having both configurations of the chiral carbons, whether the compounds are supplied as isolates of a single stereoisomer or are mixtures of enantiomers and/or diastereomers. Separation of mixtures of diastereomers may be effected by any conventional means. Mixtures of enantiomers may be separated by any of the usual techniques, such as by reacting them with optically active preparations and separating the resulting diastereomers.

It should further be noted that the reaction products may be unseparated mixtures of A and B ring additions, e.g., mixtures of formulas 1 and 2 or 3 and 4 or 5 and 6. Either the separated forms, e.g., formula 3 alone or 4 alone, or mixtures in any ratio, may be used in the methods and compositions of the invention.

Further still, dimeric forms of the green porphyrin and dimeric or multimeric forms of green porphyrin/porphyrin combinations can be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

Administration of Green Porphyrin Compound

In the method of the invention, the subject is administered an amount of the green porphyrin compound or a mixture of green porphyrin compounds in one or several dosages. The dosage depends upon the purity and chemical form of the green porphyrin and the degree of absorption expected. Suitable amounts per dose are typically greater than about 0.5 mg/kg of body weight, preferably in the range of from about 0.5 to 5.0 mg/kg per dose, and most preferably is about 0.5 to 2.0 mg/kg per dose. These dosage ranges are intended to be suggestive and should not necessarily be considered as limiting, since the individual reactions of particular subjects will vary. Adjustment of the dosage ranges in accordance with individual variations is routine among practitioners.

Similarly, no single protocol appears to be desirable for all cases at this time. However, typical protocols will include either a single dose or an initial dose followed by 1–4 additional doses at weekly, biweekly or monthly intervals. A particularly preferred protocol calls for 3 doses about two weeks apart. Again, these protocols are not intended to be limiting in view of the wide variation permitted in protocol design.

The green porphyrin compounds of the invention may be administered as a single compound, preferably BPD-MA, or as a mixture of various green porphyrins. Suitable formulations include those appropriate for systemic administration, including preparations for injection, transmucosal or transdermal administration, or oral administration. A particularly preferred means of formulating the green porphyrin of the invention for this use is in the form of a solution or as liposomes suitable for injection into a peripheral vein. The green porphyrin may be included within the liposomes, attached to their surface, or both. Suitable methods for preparing liposomes are well-known in the art. The inclusion of green porphyrin compounds in such preparation is described, for example, in Allison et al., U.S. Pat. No. 5,214,036 issued 25 May 1993 and published European Patent Specification EP 0 569 113 B1, both of which are incorporated herein by reference.

When injected intravenously, the solution or liposome formulation disseminates throughout the vascular system and thus comes into direct contact with the arterial plaques being targeted, where the green porphyrin is selectively absorbed, with peak concentration typically occurring within about 24 hours. The presence of green porphyrin in the plaque may be detected within a few hours after injection and may persist for as long as several days to two weeks.

In one embodiment, the absorption of green porphyrins by atheromatous plaques may be enhanced by binding to the green porphyrin some antibody specific to a component of the plaque. Monoclonal antibodies may be particularly useful due to their extreme specificity. Components of plaque that can serve as antigenic targets include elastic elements, collagen, and lipid constituents.

In the methods of the invention, the green porphyrin compounds, formulated into pharmaceutical compositions, are administered without the need to irradiate invasively at the site of the potential or growing arterial plaque with light that is absorbed by the green porphyrin. The expression "in the absence of irradiation with light absorbed by the green porphyrin" is intended to mean that no such deliberate irradiation is administered. The phrase does not, of course, exclude inadvertent, coincidental, or normal exposure of the affected tissues to ambient light.

The following examples are intended to illustrate but not to limit the invention.

EXAMPLE 1

Dose Variations

This study was performed to assess the effect of liposomal BPD-MA green porphyrin on the development of aortic fatty plaque in rabbits fed a high fat diet. Twenty test animals were selected and divided into four groups. Throughout the study, all animals were maintained on a diet consisting of re-pelleted rabbit chow containing 7% corn oil and 1.5% cholesterol. Three of the groups were dosed with either 0.5, 1.0 or 2.0 mg/kg of BPD-MA at two weeks and at six weeks after the start of the high fat diet. The fourth group of animals received no BPD-MA at all and thus served as a control group. All test animals were necropsied at 7 weeks, and their aortas were dissected out and fixed for macroscopic and microscopic examination by a certified veterinary pathologist. Histopathology was carried out on formalin-fixed sections using standard haematoxylin and eosin staining techniques. Data from the five individual animals in each test group was averaged to obtain the values for the group.

In the macroscopic assessment, whole rabbit aortas of about 15 cm in length were examined for the severity and extent of plaque. The results are summarized below in Table 1.

TABLE 1

| Group | Drug Dose (mg/kg) | Severity[1] | Extent of Affected Tissues[2] (cm) | % of Affected Tissues |
|---|---|---|---|---|
| 1 | 0 | 2.2 | 7.0 | 46.7 |
| 2 | 0.5 | 1.8 | 2.5 | 16.7 |
| 3 | 1.0 | 1.3 | 4.8 | 32.0 |
| 4 | 2.0 | 1.2 | 0.9 | 6.1 |

[1]Severity:
0 = No plaque.
1 = Small linear plaques (3 mm or less).
2 = Confluent areas of plaque involving less than ½ of the arterial circumference.
3 = Confluent areas of plaque involving more than ½ of the arterial circumference.
[2]Extent: The total length of the aorta in linear cm that was affected by plaque. Where several separate areas were involved, the lengths affected were added to give a total value.

A section of rabbit aorta approximately 1 cm from the aortic bifurcation was taken for microscopic examination. This particular portion of the aorta was selected because it is generally considered to best represent overall plaque development. The results are summarized below in Table 2.

TABLE 2

| Group | Drug Dose (mg/kg) | Severity of Plaque[1] | No. Sections Containing Aortic Plaque |
|---|---|---|---|
| 1 | 0 | 1.0 | 4/5 |
| 2 | 0.5 | 0.8 | 3/5 |
| 3 | 1.0 | 0.2 | 1/5 |
| 4 | 2.0 | 0 | 0/5 |

[1]Severity:
0 = Normal aorta.
1 = One or more sub-endothelial fatty plaques with less than 30% of the aortic section involved.
2 = Sub-endothelial fatty plaques with 30–60% of the section affected.
3 = Sub-endothelial fatty plaques with greater than 60% of the section affected.

Both the severity of plaque and the extent of plaque-affected tissue appeared to decrease with increasing doses of BPD-MA. These effects were observed both macroscopically and microscopically. In both cases, the greatest effect was seen in the animals that received 2.0 mg/kg of the green porphyrin.

EXAMPLE 2

Variation of Number of Doses

In this study, two groups of test animals (n=6 per group) were dosed with 2 mg/kg of BPD-MA at either two weeks after the start of the high fat diet described above in Example 1 or at two, four and six weeks after the start of the diet. A third group served as a control group and, thus, received no BPD-MA. All animals were necropsied at 8 weeks, and the rabbit aortas were dissected out and fixed as described above in Example 1.

Macroscopic examination was carried out on aortas ranging from about 13.0 to 17.5 cm in length. The results are presented below in Table 3:

TABLE 3

| Group | Drug Dose | Time of Drug Dose from Start of Diet (weeks) | Severity[2] | Extent of Affected Tissue[2] | % of Affected Tissue |
|---|---|---|---|---|---|
| 1 | 0 | 0 | 2.2 | 5.0 | 30.6 |
| 2 | 2.0 | 2 | 1.7 | 2.5 | 17.8 |
| 3 | 2.0 | 2, 4, 6 | 1.2 | 0.9 | 5.9 |

[1]and[2]: See Table 1.

Sections of rabbit aorta were also taken for microscopic examination at approximately 1, 2 and 3 cm from the aortic bifurcation. The 1-cm section was considered to be comparable to the section taken in Example 1. The results are summarized below in Table 4:

TABLE 4

| Group | Drug Dose (mg/kg) | Time of Drug Dose from Start of Diet (weeks) | Severity of Plaque[1] (Sections 1, 2, 3 cm) | No. Sections Containing Aortic Plaque (Sections 1, 2, 3) |
|---|---|---|---|---|
| 1 | 0 | 0 | 1.3, 1.7, 2.2 | 4/6, 5/6, 5/6 |
| 2 | 2.0 | 2 | 0.8, 1.0, 2.0 | 4/6, 4/6, 5/5 |
| 3 | 2.0 | 2, 4, 6 | 0.7, 1.3, 2.0 | 2/6, 5/6, 5/6 |

[1]See Table 2.

The results from both the macroscopic and microscopic examinations indicated a decrease in the severity and extent of aortic plaque after a single dose of BPD-MA six weeks before the end of the study. After three repeated doses of drug at two-week intervals, however, the decreases appeared to be even more pronounced.

We claim:

1. A method to treat arterial plaque in a subject, said method comprising the steps of:
    a. administering to said subject, in one or more doses, an amount of green porphyrin compound effective to accomplish said treatment; and
    b. allowing said treatment to occur in the absence of purposeful irradiation with light.

2. The method of claim 1 wherein from one to five doses of green porphyrin are administered.

3. The method of claim 2 wherein one dose is administered.

4. The method of claim 2 wherein three doses are administered.

5. The method of claim 1 wherein said effective amount is greater than 0.5 mg/kg in each dose.

6. The method of claim 5 wherein said effective amount is from 0.5 to 5.0 mg/kg in each dose.

7. The method of claim 5 wherein said effective amount is from 0.5 to 2.0 mg/kg in each dose.

8. The method of claim 1 wherein said green porphyrin is administered in a liposomal formulation.

9. The method of claim 1 wherein said green porphyrin is selected from the group consisting of:

-continued wherein $R^1$, $R^2$, $R^3$ and $R^4$ are non-interfering substituents.

10. The method of claim 9 wherein $R^1$ and $R^2$ are independently carbomethoxy or carboethoxy.

11. The method of claim 9 wherein each $R^3$ is —$CH_2CH_2COOH$ or a salt, amide, ester or acyl hydrazone thereof.

12. The method of claim 9 wherein said green porphyrin has the formula 3 or 4.

13. The method of claim 12 wherein said green porphyrin is selected from the group consisting of BPD-DA, BPD-DB, BPD-MA and BPD-MB.

14. The method of claim 13 wherein said green porphyrin is BPD-MA.

15. The method according to claim 1 wherein said treatment is conducted under conditions of exposure to ambient light.

16. A method to treat arterial plaque in a subject that comprises administering, in the absence of purposeful irradiation with light, one or several doses of a pharmaceutical composition, itself comprising:

a. a unit dosage amount of a green porphyrin compound; and b. a pharmaceutically acceptable excipient.

17. The method of claim 16 wherein said composition is administered in one to five doses.

18. The method of claim 17 wherein said composition is administered in one dose.

19. The method of claim 17 wherein said composition is administered in three doses.

20. The method according to claim 16 wherein said treatment is conducted under conditions of exposure to ambient light.

* * * * *